United States Patent
Zaleski (10) Patent No.: US 7,945,457 B2
(45) Date of Patent: May 17, 2011

(54) DISTRIBUTED SYSTEM FOR MONITORING PATIENT VIDEO, AUDIO AND MEDICAL PARAMETER DATA

(75) Inventor: John R. Zaleski, Elkton, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 515 days.

(21) Appl. No.: 12/062,622

(22) Filed: Apr. 4, 2008

(65) Prior Publication Data

US 2008/0249801 A1 Oct. 9, 2008

Related U.S. Application Data

(60) Provisional application No. 60/911,302, filed on Apr. 12, 2007, provisional application No. 60/910,674, filed on Apr. 9, 2007.

(51) Int. Cl.
*G06Q 10/00* (2006.01)
(52) U.S. Cl. ............... 705/2; 705/3; 705/4; 600/300
(58) Field of Classification Search ............... 600/300; 340/7.29
See application file for complete search history.

(56) References Cited

U.S. PATENT DOCUMENTS

| 5,942,986 | A | 8/1999 | Shabot et al. |
| 6,322,502 | B1 | 11/2001 | Schoenberg et al. |
| 6,804,656 | B1 * | 10/2004 | Rosenfeld et al. ............ 705/3 |
| 7,756,723 | B2 * | 7/2010 | Rosow et al. ............ 705/2 |
| 2004/0019900 | A1 * | 1/2004 | Knightbridge et al. ......... 725/23 |

* cited by examiner

*Primary Examiner* — Linh Michelle Le
(74) *Attorney, Agent, or Firm* — Alexander J Burke (57) ABSTRACT

A distributed patient monitoring system visually monitors patients and patient parameters using multiple portable processing devices. The system includes an authentication processor enabling a user to obtain access authorization to access patient data. A clinical application display image identifies multiple different patients in corresponding multiple different locations and enables a user to select a particular patient. A data processor uses access information in acquiring live video and vital sign parameters of the particular patient from a room associated with the particular patient. A display processor initiates generation of data representing an image sequence comprising a composite image including a first area showing acquired live video of the particular patient and a second area presenting acquired vital sign parameters of the particular patient using the clinical application display image.

15 Claims, 5 Drawing Sheets

DISTRIBUTED SYSTEM FOR MONITORING PATIENT VIDEO, AUDIO AND MEDICAL PARAMETER DATA

This is a non-provisional application of provisional application Ser. No. 60/910,674 filed Apr. 9, 2007 and of provisional application Ser. No. 60/911,302 filed Apr. 12, 2007, by J. R. Zaleski.

FIELD OF THE INVENTION

This invention concerns a system for use by a portable processing device operating in a distributed patient monitoring system for visually monitoring patients and patient parameters using multiple portable processing devices in different remote locations.

BACKGROUND OF THE INVENTION

Known patient monitoring systems (e.g., Intensive Care Unit (ICU) monitoring systems as described in U.S. Pat. No. 6,804,656) employ a single command center. Patient information is transmitted from multiple patient rooms to a single viewer (that is, display device) and audio reproduction device located in a single centralized command center. In this system a user needs to be physically located within the command center to view and interact with information transmitted from individual patient rooms within an intensive care unit (ICU). A system according to invention principles addresses these deficiencies and related problems.

SUMMARY OF THE INVENTION

The inventors have recognized that acquiring and displaying patient video, audio and medical parameter information using multiple remotely located personal computing devices of clinicians poses a number of problems. Specifically, difficulties are involved in supporting bidirectional communication enabling identification and acquisition of patient video, audio and medical parameter information for particular patients from multiple patient rooms for communication to multiple remotely located processing devices. Further difficulties are encountered in providing the high volume information in a flexible, secure manner using bandwidth limited communication channels.

A system provides a networking and processing architecture for communicating video and audio information to and from patient rooms using standard (e.g., Ethernet) networking and analyzes, processes and displays video and audio information on multiple distributed wired or wirelessly operating computing platforms (portable or fixed processing devices). A system for use by a portable processing device operating in a distributed patient monitoring system for visually monitoring patients and patient parameters uses multiple portable processing devices in different remote locations. The system includes an authentication processor enabling a user to obtain access authorization to access patient data in response to entry of identification data using a portable processing device of the multiple portable processing devices in different remote locations. A user interface, in response to the access authorization, enables a user to, initiate execution of a clinical information system providing a user with a clinical application display image identifying multiple different patients in corresponding multiple different locations and select a particular patient of the multiple different patients in the clinical application display image. A data processor uses an identifier of the particular patient in acquiring access information associated with the particular patient from a repository and uses the access information in acquiring live video and vital sign parameters of the particular patient from a room associated with the particular patient. A display processor initiates generation of data representing an image sequence comprising a composite image including a first area showing acquired live video of the particular patient and a second area presenting acquired vital sign parameters of the particular patient in response to user selection of an image element associated with the particular patient of the multiple different patients in the clinical application display image.

DETAILED DESCRIPTION OF THE INVENTION

A system according to invention principles employs an architecture that enables a user (clinician) to request a video and audio feed from one or more user selected patients from cameras and microphones contained within patient rooms within a hospital or hospital enterprise and to display the video and listen to the audio on a wireless laptop (or other fixed or mobile processing device). Patients are selected for viewing and listening and patient parameter monitoring via a health information system Web browser user interface on any one of multiple portable (or fixed location) processing devices located in or outside of a healthcare provider enterprise, for example. Patient selection is advantageously automatic and context based, in which the video and audio of a patient are selected automatically on the basis of the currently open patient medical record.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 5) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

Figure 1:
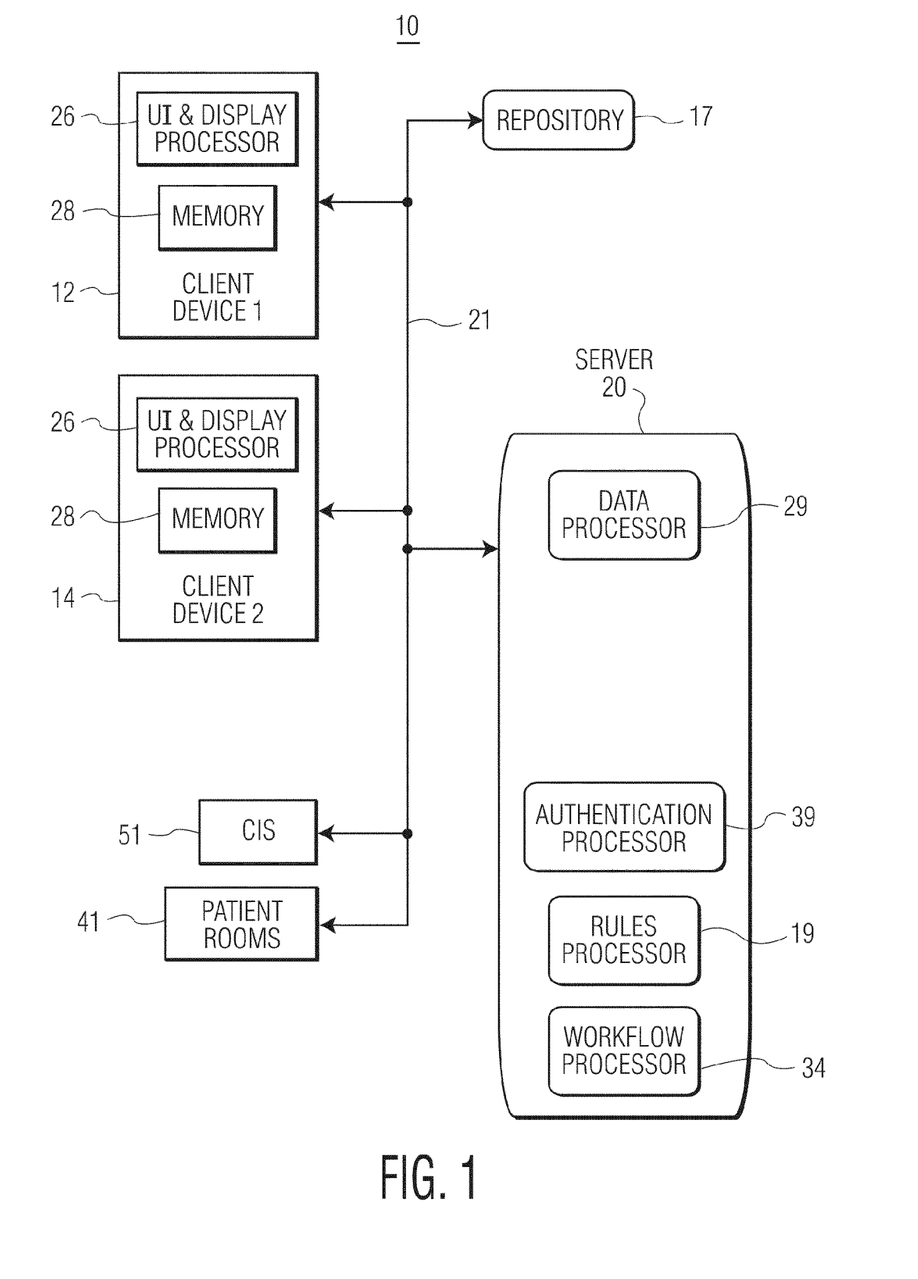
FIG. 1 shows a system for use by a portable processing device operating in a distributed patient monitoring system for visually monitoring patients and patient parameters, according to invention principles.

FIG. 1 shows system 10 for use by portable processing devices 12 and 14 operating in a distributed patient monitoring system for visually monitoring patients and patient parameters in patient rooms 41 in different remote locations. System 10 includes portable devices (e.g., notebooks, Personal Digital Assistants, cell phones) 12 and 14, at least one repository 17, Clinical or enterprise-wide Health Information System Application (CIS) 51 and server 20 as well as devices (including cameras and patient monitoring devices) in patient rooms 41, inter-communicating via network 21. Portable devices 12 and 14 individually include memory 28 and user interface and user interface 26. User interface and display processor 26 provides data representing display images for presentation on portable device 12 and 14.

Server 20 includes data processor 29, authentication processor 39, workflow processor 34 and rules processor 19. Authentication processor 39 enables a user to obtain access authorization to access patient data in response to entry of identification data using portable processing device 12 of the multiple portable processing devices in different remote locations. User interface 26, in response to the access authorization, enables a user to, initiate execution of clinical information system 51 providing a user with a clinical application display image identifying multiple different patients in corresponding multiple different locations and select a particular patient of the multiple different patients in the clinical application display image. Data processor 29 uses an identifier of the particular patient in acquiring access information associated with the particular patient from repository 17 and uses the access information in acquiring live video and vital sign parameters of the particular patient from a room associated with the particular patient.

User interface 26 initiates generation of data representing an image sequence comprising a composite image including a first area showing acquired live video of the particular patient and a second area presenting acquired vital sign parameters of the particular patient in response to user selection of an image element associated with the particular patient of the multiple different patients in the clinical application display image. Workflow processor 34 initiates, tracks and monitors task sequences performed by personnel and systems in response to events. Rules processor 19 applies rules to the vital sign parameters to identify an alert condition indicating a significant patient clinical condition or change of clinical condition and the composite image includes an image element indicating the alert condition. Communication network 21 has bandwidth sufficient to communicate processed video data to portable processing devices 12 and 14 respectively of the multiple different portable processing devices in different remote locations in response to commands received from the first and second portable processing devices 12 and 14 respectively.

Figure 2:
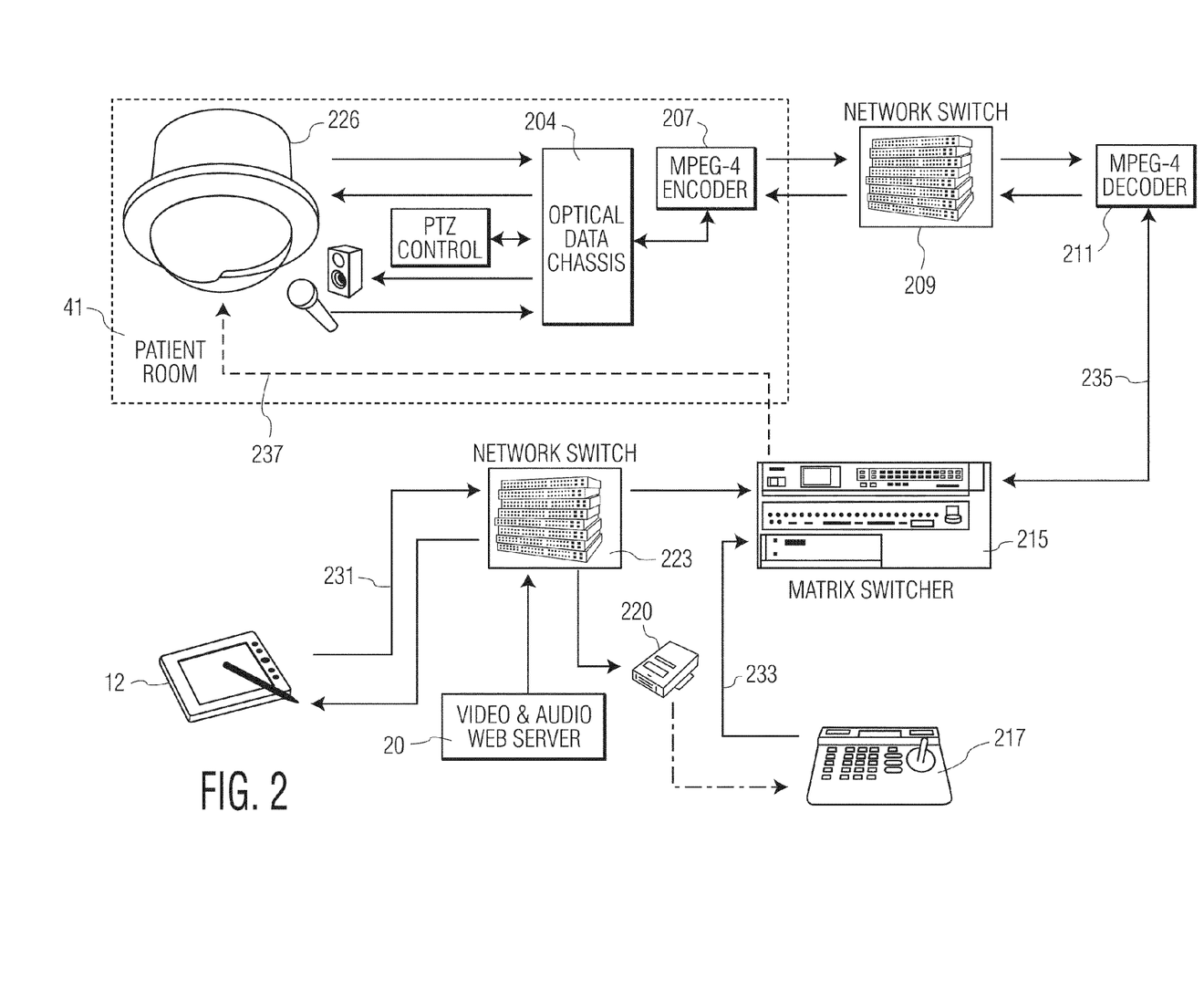
FIG. 2 shows an architecture and functional operation of the system for use by portable processing devices, according to invention principles.

FIG. 2 shows an architecture and functional operation of system 10 for use by portable processing devices. In response to user selection of a particular patient in a clinical application display image provided on portable processing device 12 by user interface 26, a parameter is acquired from a medical record of a patient and provided in a URL data field to a Web-enabled plug-in (such as a Plug-in or other executable procedure, such as an ActiveX component) in server 20 (or in another embodiment in portable processing device 12), for example. The Plug-in employs a decoder 211 for decoding video in MPEG-4 (or other) compressed format and displaying the video on portable processing device 12 through a live browser. The Plug-in compares a patient location (specified in terms of room and bed identifier) with an existing database associating patient room identifiers, camera identifiers an identifier of a particular camera of the patient room concerned. A one-to-one mapping between room and bed and camera is maintained within a common master file in repository 17. The Plug-in instructs a camera controller to retrieve the video and audio information for the particular camera. Video data, audio data and patient parameter information are routed to the Plug-in which initiates display of a picture and communicates audio data directly to a user wireless computing platform (portable device 12). An authorized user may view any patient concurrently with other users using the communication architecture of FIG. 2 and users may analyze the video image and communicate via bidirectional audio link with personnel located within a specific patient's room. Users may also control the angle, iris and focus of cameras within any patient room via a virtual pan-tilt-zoom (PTZ) control that is displayed within the Web browser of user portable processing device 12 and a data entry device controller 217. The virtual pan-tilt-zoom (PTZ) control is implemented in an executable procedure of the Plug-in. The system may be employed in any room within a hospital and patient video, audio and medical parameter information can be viewed by any authorized clinician via a Web browser without the need to be at any one physical location (e.g., command center or central command station) within the hospital enterprise. The system architecture enables a remotely located authorized user to display room video and interact with personnel within a patient room and allows users to concurrently monitor video of a patient and patient parameters via a Web browser and to communicate with personnel from within a hospital.

Figure 3:
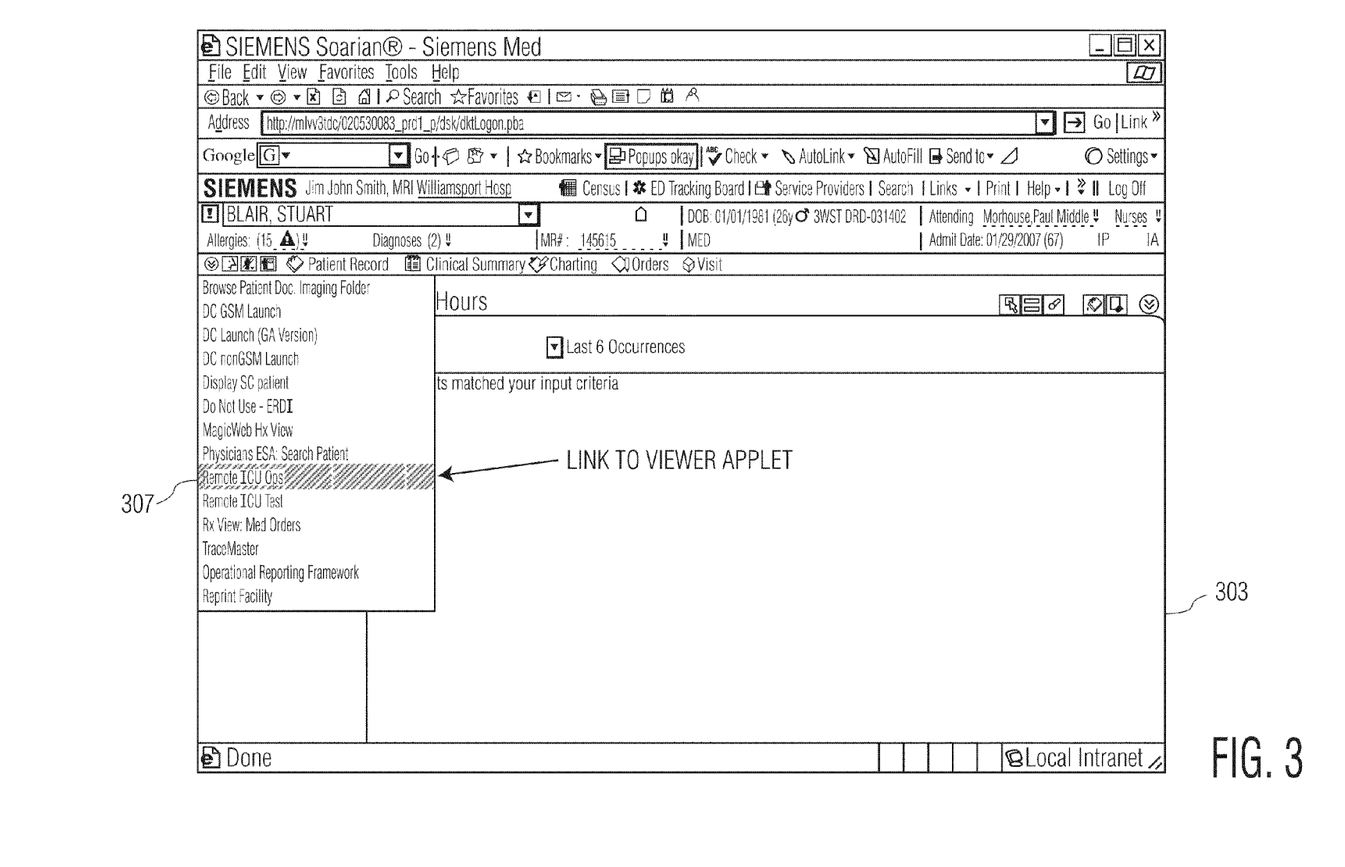
FIG. 3 shows a Web-browser compatible user interface display image window enabling a user to initiate visual monitoring of one or more patients and associated sets of patient parameters via an applet, for example, according to invention principles.

In the FIG. 2 embodiment, a user displays patient record data downloaded from a repository (e.g. repository 17 FIG. 1 (not shown in FIG. 2 to preserve drawing clarity)) via network 21 and switch 223 using a Plug-in that interoperates with a Video & Audio Web Server 20. The patient record data is displayed via a Web browser on wireless computing platform 12. The displayed patient record data includes a URL link to a camera viewer applet in server 20 such as an external URL link represented by item 305 as illustrated in display image 303 of FIG. 3. Specifically, FIG. 3 shows Web-browser compatible user interface display image 303 enabling a user to initiate visual monitoring of one or more patients and associated sets of patient parameters via an applet, for example. In response to user selection of URL link 305, execution of the Plug-in in server 20 is initiated and patient room and bed location identifiers associated with the clinical record are provided to the Applet via URL parameters. Exemplary URL syntax is: http://localhost/optelecom/asp/searchDbase.asp?mrn=400607&loc=050101

The parameter field "loc" designates a room and bed location identifier of a particular patient. The parameter field "mrn" designates the medical record number associated with the particular patient. The values shown here are exemplary only. The active server page "searchDbase.asp" indicated in the URL comprises an executable software procedure that locates a camera identifier and identifiers of patient monitoring devices associated with a patient having a room and bed location specified by "loc" data and passes this information to the Plug-in. Also, in response to a user initiating execution of the Plug-in within the client browser on portable processing device 12, a display image is presented enabling a user to control a camera in a patient room via the virtual pan-tilt-zoom (PTZ) capability. A PTZ command 231 is transmitted from device 12 to matrix switch 215 via network switch 223 in TCP/IP protocol over Ethernet in response to user interaction with the Applet. The PTZ commands are communicated over Ethernet to an Ethernet-to-serial converter 220 which controls a PTZ remote controller 217 that issues commands to Matrix Switch 215 via RS-422 link 233. Matrix Switch 215 converts commands and data for bidirectional exchange with specific camera 226 over optical fiber, for example. Video, audio and control data 235 is conveyed using TCP/IP over Ethernet, for example, between patient room 41 devices (camera, microphone, PTZ control unit and sound reproduction unit) via optical data channel unit 204 and matrix switch 215 via MPEG4 encoder 207 (encoding video data into MPEG4 format), network switch 209 and MPEG4 decoder 211 (decoding MPEG4 data into video data) and optical fiber link 235. Commands and data are transmitted to a PTZ function control unit internal to camera 226 to enable a remotely located user to control the camera. Further, power to camera 226 is conveyed via cable 237.

Figure 4:
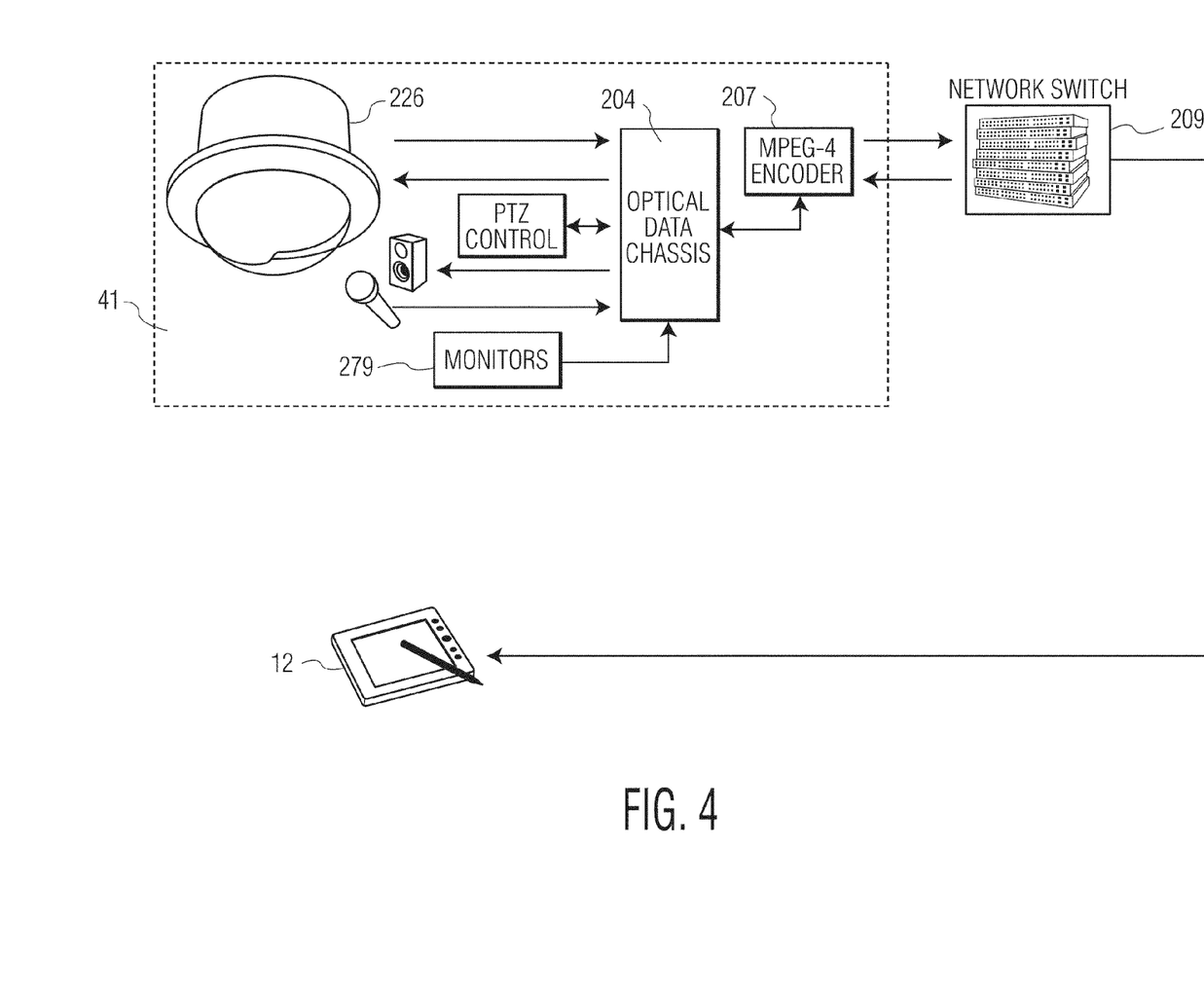
FIG. 4 further illustrates a networked architecture embodiment and components of a system for use by a portable processing device, according to invention principles.

FIG. 4 further illustrates a networked architecture embodiment and components of a system for use by a portable processing device. In response to a user operating the virtual pan-tilt-zoom (PTZ) function of camera 226 via a display image presented on portable processing device 12, the camera transmits video data via optical fiber (or other relatively high bandwidth channel) to MPEG4 encoder 207 through distribution unit 204. Encoded video data is communicated via network switch 209 to an MPEG4 decoder in portable processing device 12 for decoding and presentation to a user. The outbound transmission of the audio and video data of a patient and patient parameters is illustrated in the architecture shown in FIG. 4. Data comprising compressed video images is transmitted via TCP/IP over Ethernet, for example, to a Web browser-based executable procedure (e.g., a Plug-in) of a remotely located portable processing device 12 for display to a user. The Ethernet-based communication link and the remote control capability of camera 226, enables video to be displayed remotely to any user at any location within an enterprise as long as network connectivity is available. If a high bandwidth wireless or other communication link is available, the video and audio data and patient parameter information is transmitted to users outside of the healthcare enterprise buildings. The MPEG-4 communication reduces the traffic rate across a network to a maximum of 2000 Kilobits per second (at a camera frame rate of 30 per second) in one implementation, for example. This is within the networking capacity of a 100 Megabit per second Ethernet backbone.

The communication network linking the elements of the FIG. 4 embodiment has bandwidth sufficient to communicate vital sign parameters and associated video data representative of multiple sequences of video images of corresponding multiple different patients from patient rooms 41 to multiple different portable processing devices (e.g., 12 and 14 of FIG. 1) in different remote locations in response to commands received from the multiple different portable processing devices. Switch 209 routes acquired vital sign parameters and associated video data of a particular patient of the multiple different patients to a particular processing device of the multiple different portable processing devices via the communication network in response to user command entered using particular processing device 12. The user command comprises user selection of an image element (e.g., a hyperlink) associated with the particular patient in a display image provided by a clinical information system application. The image element associated with the selected patient is presented in a list of different patients in the display image provided by a clinical information system application.

Multiple patient monitoring devices (e.g., devices 279) provide vital sign parameters of multiple different patients. Further, multiple video cameras (e.g., camera 226) in rooms associated with the multiple different patients provide the associated video data. Encoder 207 processes the associated video data to provide processed video data for communication using switch 209 and the communication network by encoding the video data with a compression function compatible with MPEG-4, MPEG-2 or DIVX, for example. Encoder 207 processes the audio data to provide processed audio data by encoding the audio data with a compression function. The communication network communicates audio data from patient rooms to the multiple different portable processing devices and switch 209 routes acquired audio data of a particular patient to the particular processing device via the communication network in response to user command entered using the particular processing device. The audio data is provided by multiple different microphones in patient rooms associated with the multiple different patients.

Figure 5:
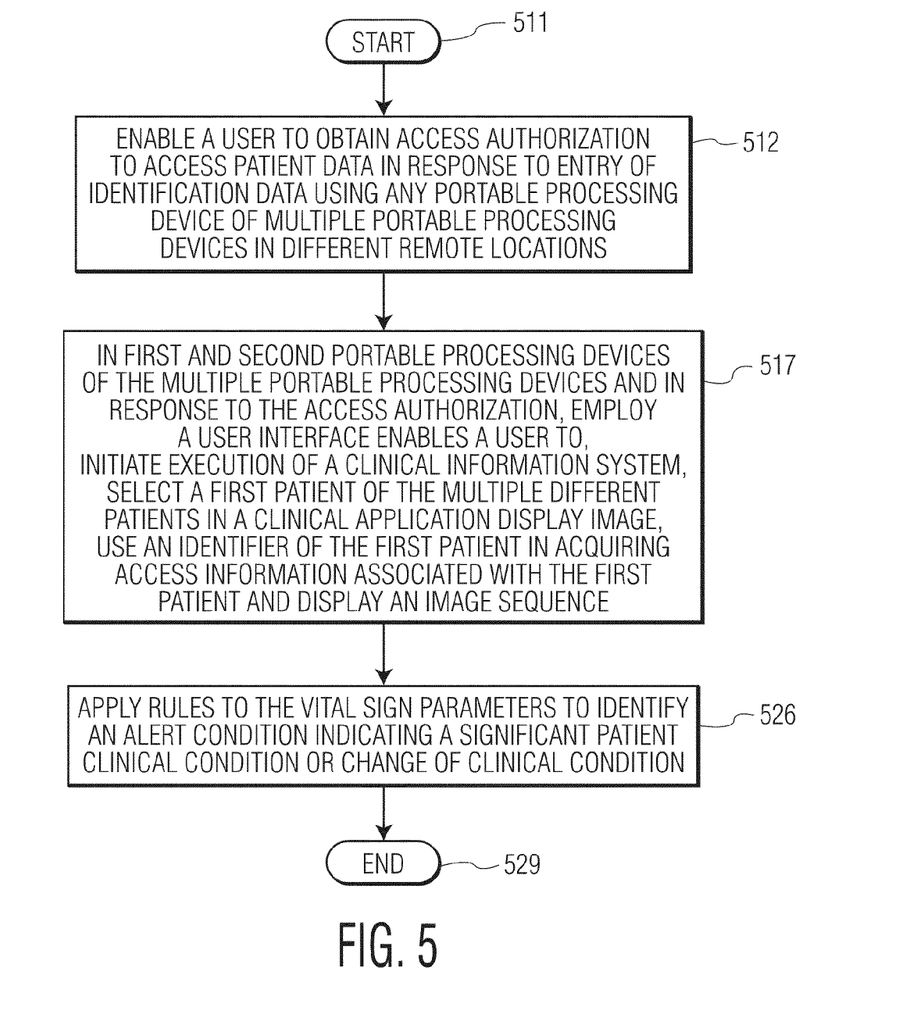
FIG. 5 shows a flowchart of a process performed by a portable processing device operating in a distributed patient monitoring system, according to invention principles.

FIG. 5 shows a flowchart of a process performed by multiple portable processing device operating in a distributed patient monitoring system in a remote location operating in a distributed patient monitoring system for visually monitoring patients and patient parameters. In step 512 following the start at step 511, authentication processor 39 (FIG. 1) enables a user to obtain access authorization to access patient data in response to entry of identification data using any portable processing device of the multiple portable processing devices in different remote locations. First portable processing device 12 of the multiple portable processing devices and responsive to the access authorization, includes a user interface enabling a user in step 517 to, initiate execution of a clinical information system providing a user with a clinical application display image identifying multiple different patients in corresponding multiple different locations. The user interface enables a user to select a first patient of the multiple different patients in the clinical application display image. The user interface uses an identifier of the first patient in acquiring access information associated with the first patient from a repository and uses the access information in acquiring live video and vital sign parameters of the first patient from a room associated with the particular patient. The user interface enables a user to display an image sequence including a composite image comprising a first area showing live video of the first patient and a second area presenting vital sign parameters of the first patient.

Similarly, second portable processing device 14 of the multiple portable processing devices and responsive to the access authorization, includes a user interface enabling a user, concurrently with operation of first portable processing device 12, to, initiate execution of a clinical information system providing a user with a clinical application display image identifying multiple different patients in corresponding multiple different locations. The user interface enables a user, concurrently with operation of first portable processing device 12, to select a second patient of the multiple different patients in the clinical application display image. The user interface uses an identifier of the second patient in acquiring access information associated with the second patient from a repository and uses the access information in acquiring data representing live video and vital sign parameters of the second patient from a room associated with the particular patient. The user interface displays an image sequence including a composite image comprising a first area showing live video of the second patient and a second area presenting vital sign parameters of the second patient. In step 526 rules processor 19 applies rules to the vital sign parameters to identify an alert condition indicating a significant patient clinical condition or change of clinical condition and first portable processing device 12 provides a display image indicating the alert condition. The process of FIG. 5 terminates at step 529.

The systems and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system network and communication architecture supports remote control and viewing of patients within a healthcare enterprise. Multiple users may view the same patients concurrently from any location within a hospital network via a Web browser-based application, for example. The system network and structural architecture supports communicating, viewing and analyzing substantially real-time or near real-time video images of patients within a healthcare enterprise. The system is of particular use when operating in conjunction (or integrated) with a clinical information system. The processes and applications may in alternative embodiments, be located on one or more (e.g., distributed) processing devices accessing a network linking the elements of FIG. 1. Further, any of the functions and steps provided in FIGS. 1-5 may be implemented in hardware, software or a combination of both and may reside on one or more processing devices located at any location of a network linking the elements of FIG. 1 or another linked network including the internet.

What is claimed is:

1. A system for use by a portable processing device operating in a distributed patient monitoring system for visually monitoring patients and patient parameters using a plurality of portable processing devices in different remote locations, comprising:
   an authentication processor enabling a user to obtain access authorization to access patient data in response to entry of identification data using a portable processing device of said plurality of portable processing devices in different remote locations;
   a user interface, in response to said access authorization, enabling a user to,
      initiate execution of a clinical information system providing a user with a clinical application display image identifying a plurality of different patients in a corresponding plurality of different locations and
      select a particular patient of said plurality of different patients in said clinical application display image;
   a data processor for using an identifier of said particular patient in acquiring access information associated with said particular patient from a repository and using said access information in acquiring live video and vital sign parameters of said particular patient from a room associated with said particular patient via a switch for routing vital sign parameters and video data of said plurality of different patients to said plurality of portable processing devices; and
   a display processor for initiating generation of data representing an image sequence comprising a composite image including a first area showing acquired live video of said particular patient and a second area presenting acquired vital sign parameters of said particular patient in response to user selection of an image element associated with said particular patient of said plurality of different patients in said clinical application display image.

2. A system according to claim 1, including
   a rules processor for applying rules to said vital sign parameters to identify an alert condition indicating a significant patient clinical condition or change of clinical condition and wherein said composite image includes an image element indicating said alert condition.

3. A system for use by a plurality of portable processing devices in different remote locations operating in a distributed patient monitoring system for visually monitoring patients and patient parameters, comprising:
- an authentication processor enabling a user to obtain access authorization to access patient data in response to entry of identification data using any portable processing device of said plurality of portable processing devices in different remote locations;
- a first portable processing device of said plurality of portable processing devices and responsive to said access authorization, having a user interface enabling a user, to,
    - initiate execution of a clinical information system providing a user with a clinical application display image identifying a plurality of different patients in a corresponding plurality of different locations,
    - select a first patient of said plurality of different patients in said clinical application display image,
    - use an identifier of said first patient in acquiring access information associated with said first patient from a repository and using said access information in acquiring data representing live video and vital sign parameters of said first patient from a room associated with said particular patient via a switch for routing vital sign parameters and video data of said plurality of different patients to said plurality of portable processing devices and
    - display an image sequence including a composite image comprising a first area showing live video of said first patient and a second area presenting vital sign parameters of said first patient.

4. A system according to claim 3, including
a rules processor for applying rules to said vital sign parameters to identify an alert condition indicating a significant patient clinical condition or change of clinical condition and
said first portable processing device provides a display image indicating said alert condition.

5. A system according to claim 3, including
a second portable processing device of said plurality of portable processing devices and responsive to said access authorization, having a user interface enabling a user, concurrently with operation of said first portable processing device, to,
    - initiate execution of a clinical information system providing a user with a clinical application display image identifying a plurality of different patients in a corresponding plurality of different locations,
    - select a second patient of said plurality of different patients in said clinical application display image
    - use an identifier of said second patient in acquiring access information associated with said second patient from a repository and using said access information in acquiring data representing live video and vital sign parameters of said second patient from a room associated with said particular patient and
    - display an image sequence including a composite image comprising a first area showing live video of said second patient and a second area presenting vital sign parameters of said second patient.

6. A distributed patient monitoring system for visually monitoring patients and patient parameters using a plurality of portable processing devices in different remote locations, comprising:
- a communication network of bandwidth sufficient to communicate vital sign parameters and associated video data representative of a plurality of sequences of video images of a corresponding plurality of different patients from patient rooms to a plurality of different portable processing devices in different remote locations in response to commands received from said plurality of different portable processing devices; and
- a switch for routing acquired vital sign parameters and associated video data of a particular patient of said plurality of different patients to a particular processing device of said plurality of different portable processing devices via said communication network in response to user command entered using said particular processing device and authorization and user selection initiated via image elements associated with the particular patient in a display image provided by a clinical information system application on a portable processing device.

7. A system according to claim 6, including
a plurality of patient monitoring devices for providing said vital sign parameters of said plurality of different patients and
a plurality of video cameras in rooms associated with said plurality of different patients for providing said associated video data.

8. A system according to claim 6,
including
a user interface and in response to access authorization, said user interface enables a user to initiate execution of said clinical information system providing a user with said display image identifying a plurality of different patients in a corresponding plurality of different locations.

9. A system according to claim 6, wherein
said image element associated with said selected patient comprises a hyperlink.

10. A system according to claim 9, wherein
said image element associated with said selected patient is presented in a list of different patients in said display image provided by a clinical information system application.

11. A system according to claim 6, including
an encoder for processing said associated video data to provide processed video data for communication using said switch and communication network by encoding said video data with a compression function.

12. A system according to claim 11, wherein
said compression function is compatible with at least one of, (a) MPEG-4, (b) MPEG-2 and (c) DIVX.

13. A system according to claim 6, wherein
said communication network communicates audio data from patient rooms to said plurality of different portable processing devices and
said switch routes acquired audio data of a particular patient to said particular processing device via said communication network in response to user command entered using said particular processing device.

14. A system according to claim 13, wherein
said audio data is provided by a plurality of different microphones in patient rooms associated with said plurality of different patients.

15. A system according to claim 13, including
an encoder for processing said audio data to provide processed audio data by encoding said audio data with a compression function.

* * * * *